United States Patent [19]
Finley et al.

[11] Patent Number: 5,961,532
[45] Date of Patent: Oct. 5, 1999

[54] SURGICAL TOOL HAVING FLEXIBLE TUBULAR INNER MEMBER MOVABLE FOR TISSUE WORKING

[75] Inventors: Marshal E. Finley, Fairfield; Barry J. Kauker, Soquel; Matthew J. Curran; Juan I. Perez, both of San Jose, all of Calif.

[73] Assignee: Stryker Corporation, Kalamazoo, Mich.

[21] Appl. No.: 08/919,565

[22] Filed: Aug. 29, 1997

[51] Int. Cl.⁶ .................................................. A61B 17/32
[52] U.S. Cl. .............................. 606/170; 604/22; 606/180
[58] Field of Search ................................. 606/170, 171, 606/174, 180; 604/22

[56] References Cited

U.S. PATENT DOCUMENTS

| | | |
|---|---|---|
| 4,646,738 | 3/1987 | Trott . |
| 5,152,744 | 10/1992 | Krause et al. . |
| 5,285,795 | 2/1994 | Ryan et al. ............................. 606/171 |
| 5,286,253 | 2/1994 | Fucci . |
| 5,322,505 | 6/1994 | Krause et al. . |
| 5,411,514 | 5/1995 | Fucci et al. . |
| 5,437,630 | 8/1995 | Daniel et al. . |
| 5,510,070 | 4/1996 | Krause et al. . |
| 5,540,708 | 7/1996 | Lim et al. . |
| 5,620,447 | 4/1997 | Smith et al. . |
| 5,643,294 | 7/1997 | Tovey et al. ............................. 606/170 |
| 5,643,303 | 7/1997 | Donahue ................................. 606/170 |
| 5,766,200 | 6/1998 | Mazurek et al. . |

*Primary Examiner*—Michael Buiz
*Assistant Examiner*—William Lewis
*Attorney, Agent, or Firm*—Flynn, Thiel, Boutell & Tanis, P.C.

[57] ABSTRACT

A surgical tool (10) for chucking in a powered surgical handpiece, comprising an outer tubular member (11) with an opening (41) at the distal portion thereof. An inner tubular member (30) is movable in the outer tubular member and comprises a bendable inner tube (36) of flexible polymer material and a tissue working tip (40) extending forward from the distal end of the inner tube. The inner tube has a radially enlarged distal opening recess (62). The tip includes a reduced outside diameter, proximally extending, annular flange fixed within the inner tube distal recess (61). The annular flange of the tip is formed with hills and valleys (63, 64). The inner wall of the inner tube that defines the recess is formed with hills (65) that seat in the valleys of the annular flange so as to lock the tip to the inner tube. The annular flange is further shaped so as to extend into the recess a distance less than the overall length of the recess. Consequently, the inner tube immediately below the end of the annular flange has a section of reduced wall thickness.

18 Claims, 6 Drawing Sheets

FIG.11

SURGICAL TOOL HAVING FLEXIBLE TUBULAR INNER MEMBER MOVABLE FOR TISSUE WORKING

FIELD OF THE INVENTION

This invention relates to a surgical tool having a flexible tubular inner member movable for tissue working.

BACKGROUND OF THE INVENTION

For certain endoscopic surgical procedures, for example arthroscopic knee surgery, surgical tools, such as cutters and burs, are commonly employed. Such tools typically include an elongate tubular outer member releasably fixable to the housing of a handpiece and containing an elongate tubular inner member movable therein by a motor in the handpiece. In many tools of this kind, the inner member is rotatable within the outer member and the distal end portion of the inner member defines a tissue working tip engagable with patient tissue through a window in the distal end portion of the tubular outer member. The tip comprises, for example, a bur, a shearing edge coactive with corresponding shearing edge in the outer member window, or other patient tissue working structure.

Tools of this type have normally been straight. However, in certain surgical procedures it is convenient if such a tool is bent at a location spaced intermediate the ends of the outer tubular member. A tool with an angled outer tubular member requires, however, that the inner tubular member be capable of flexing as it moves within the outer tubular member. This can be particularly difficult to achieve in an operational tool where the inner tubular member rotates within the outer tubular member, particularly at speeds at several thousand RPM.

Such rotary, bent (or angled or curved) tools are known.

For example, U.S. Pat. No. 5,437,630 (Daniel, et al.) assigned to Stryker Corporation, the present Assignee, discloses an inner member in which the flexible portion is not tubular but rather is, a central structure spaced radially inboard of the peripheral wall of the outer tubular member.

Examples of prior tools in which the flexible inner member is tubular include those disclosed in U.S. Pat. No. 4,646,738 (Trott) assigned to Concept, Inc. and U.S. Pat. No. 5,152,744 (Krause, et al.) assigned to Smith & Nephew Dyonics. Each employs an inner tubular member flexible portion of metal, at the bent portion of the outer tubular member. Such inner tubular members tend to be complex and expensive and it has proved difficult and may in extended use encounter problems of friction heating and metal fatigue.

U.S. Pat. No. 5,540,708 (Lim, et al.) assigned to Linvatec Corporation, discloses such a tool in which the flexible inner rotatable tubular member includes a metal tip, provided with a toothed window cooperable in rotative shearing relation with a corresponding shearing window in the distal end portion of the bent rigid outer tube. The inner tubular member further includes a proximal rigid plastic hub, the tip and hub being spaced by an elongate hollow tube of polymer material, for example PEEK (polyetheretherketone). However, in this particular prior tool, the structure of the joinder of the tip to the distal end of the polymer tube requires relatively complex machining operations on the adjacent ends of both and may limit the amount of force required to inadvertently pull the tip axially off the end of the tube.

Accordingly, it is an object of this invention to produce a bent tubular surgical tool having a movable (e.g. rotatable) inner tubular member and which overcomes certain difficulties of the prior art.

SUMMARY OF THE INVENTION

An inner tubular member for movable location in an outer tubular member of a surgical tool is of a kind for chucking in a powered surgical handpiece. The inner tubular member comprises an inner tube of flexible material capable of bending as it moves in the outer tubular member. The inner tube has a distal opening recess. A tissue working tip extends forward from the inner tube distal end. The tip has a reduced outside diameter, proximal end portion defining an annular flange fixedly received in the inner tube recess.

A method for making such an inner tubular member includes inserting the tip annular flange into the inner tube recess and fixing same therein against relative movement.

DETAILED DESCRIPTION

Figures 1, 2:
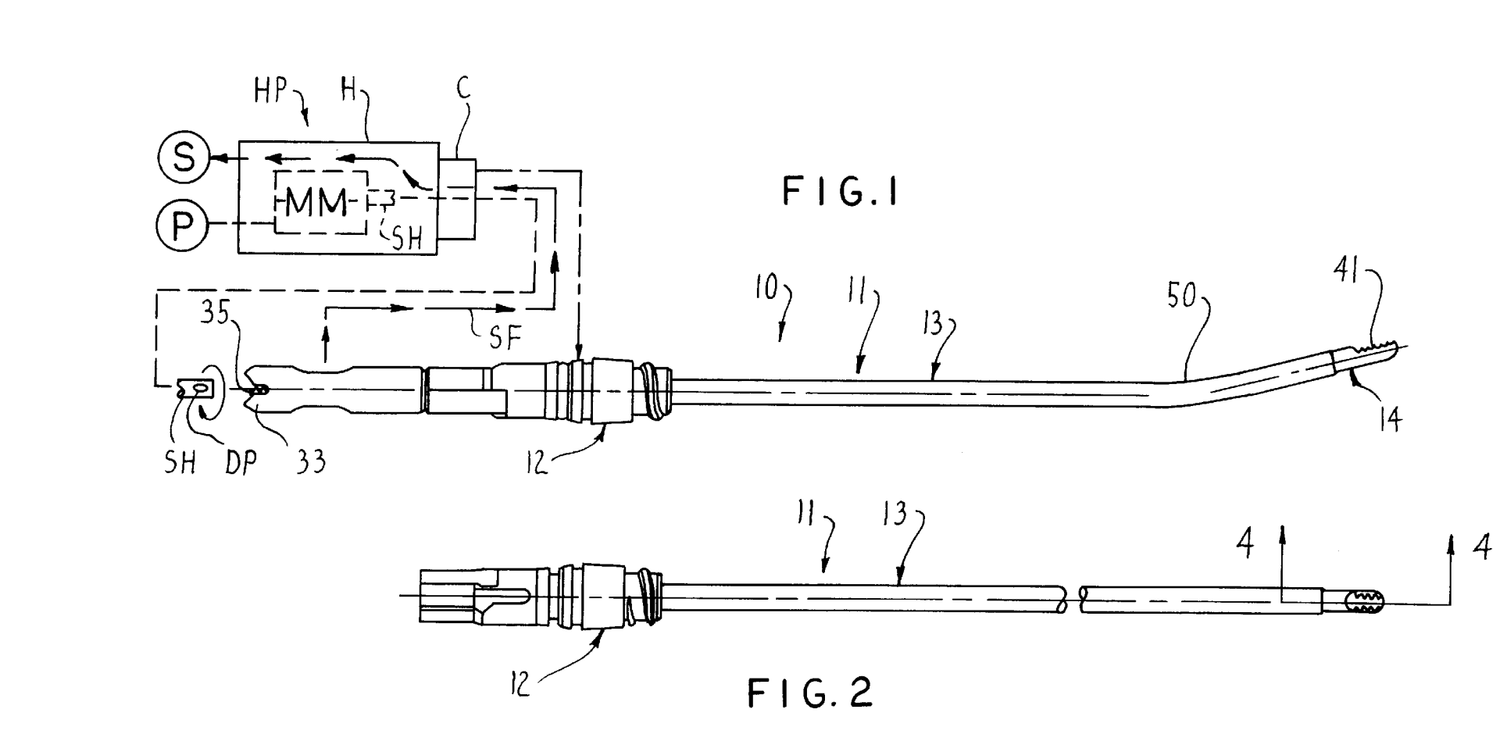
FIG. 1 is a side elevational view of a tool embodying the invention and schematically showing a handpiece engagable therewith for providing mounting, motor drive and suction connections to such tool.
FIG. 2 is a fragmentary top view of the outer tubular member of FIG. 1.
Figure 3:
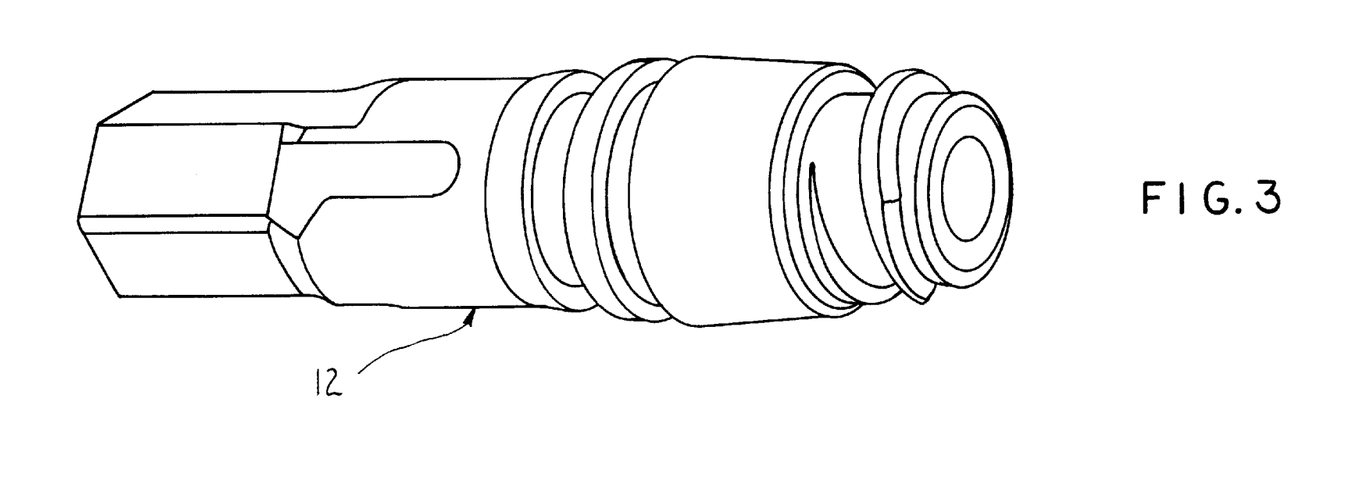
FIG. 3 is an enlarged pictorial view of the mounting hub of the FIG. 2 outer tubular member.

A tool 10 (FIG. 1) embodying the invention is adapted for chucking in a powered rotating surgical handpiece HP (FIG. 1) of any desired kind. One example of such a handpiece is disclosed in Cezana et al. U.S. Pat. No. 5,192,292 (assigned to the Assignee of the present invention). The FIG. 1 handpiece HP has a housing H fixedly containing a suitable rotary drive motor means, indicated in broken lines at MM (for example electrically or fluid powered). The motor means MM has a rotary output shaft SH extending forward therefrom and fixedly carrying at its front end a diametrally protruding drive pin DP (FIG. 1). Although the handpiece HP may contain a suitable power source, such as electric batteries, in the example shown same is connectable to a suitable remote power source P, for example an electrical power source or a pressure gas source. The handpiece HP also preferably includes a connection to a suitable suction source S.

The tool 10 comprises an outer tubular member 11 (FIG. 2) comprising a proximal hollow mounting hub 12. An elongate outer tube 13 is fixedly telescoped in and extends coaxially forwardly from the hollow mounting hub 12. The outer tube 13 includes a distal end portion 14. The outer tube 13 is for example, a rigid, thin walled, constant diameter, circular cross section tube of stainless steel or equivalent material. The mounting hub 12 is configured to be rearwardly insertable in, fixedly held by, and releasably movable forward from a chuck C on the forward end of the handpiece HP. Rearward insertion of the tool 10 into the handpiece HP (rearward insertion of the mounting hub 12 into the chuck C) fixes the outer tubular member 11 against rotation and axially with respect to the handpiece HP. The handpiece HP includes means, not shown, manually actuable to thereby allow tool 10 to be pulled forwardly out of the handpiece chuck C after surgery, or during surgery when it is desired to substitute a different tool into driving relationship with the handpiece HP.

A rotatably driven, elongate, inner tubular member 30 extends coaxially and rotatably within the outer tubular member 11 (FIG. 1). The inner tubular member 30 has a proximal end portion, defining a drive hub 31 (FIG. 6) rotatably drivably engagable by the handpiece rotary shaft SH and its transverse drive pin DP. More particularly, in the embodiment shown, the hub 31 includes at least two (here four) diametrally opposed, evenly circumferentially distributed, rearward opening notches 32 circumferentially spaced by a corresponding number of rear extending fingers 33. The notches 32 and fingers 33 surround and extend rearward from a central, blind, rear opening recess 34 in the hub 31. A coil compression spring 35 (FIG. 1) is snugly housed in the recess 34 and extends rearward therefrom.

The rotatable inner tubular member 30 includes an inner tube 36 (FIG. 6) coaxially fixed to and extending forward from the drive hub 31. The inner tube 36 is supported for rotation with the outer tube 13. The rotatable inner tubular member 30 has a distal tissue working tip 40 fixed forward on the inner tube 36 for rotation therewith and snugly rotatably disposed within the distal end portion 14 of the outer tubular member 11.

Figure 4:
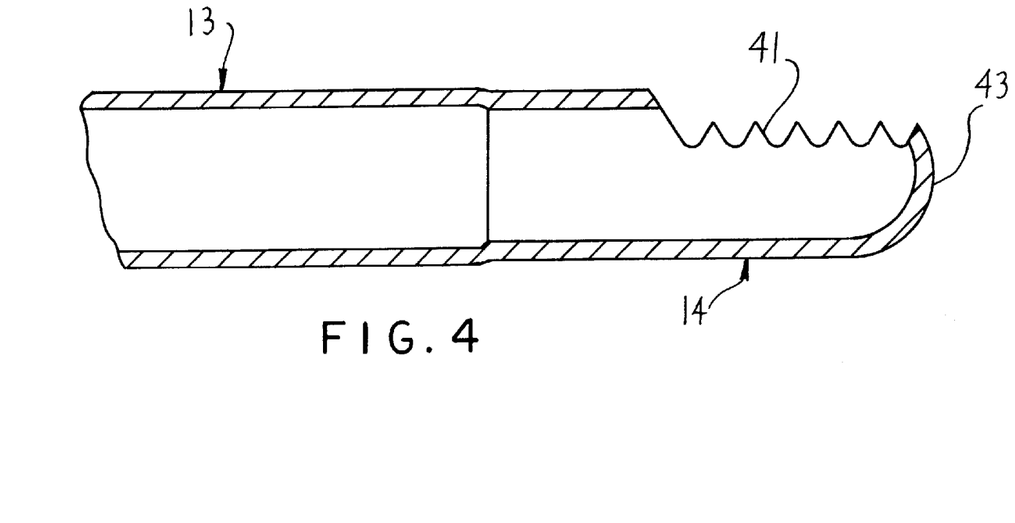
FIG. 4 is an enlarged central cross sectional view of the tip and the distal end portion of the bent tube of the FIG. 1 outer tubular member, substantially as taken on the line 4—4 of FIG. 2.
Figure 5:
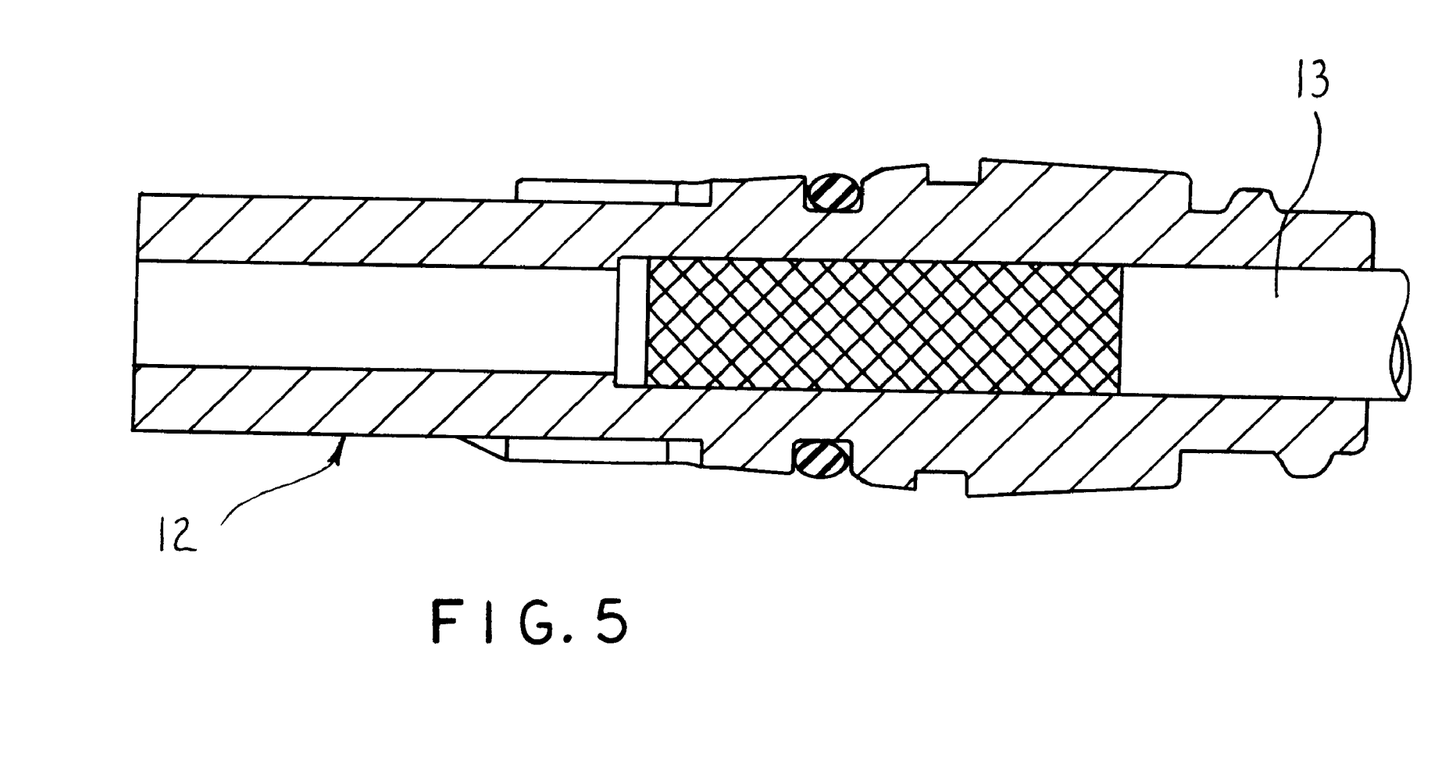
FIG. 5 is an enlarged central cross sectional view of the FIG. 1 outer tubular member mounting hub showing the outer tube mounting therein.
Figure 8:
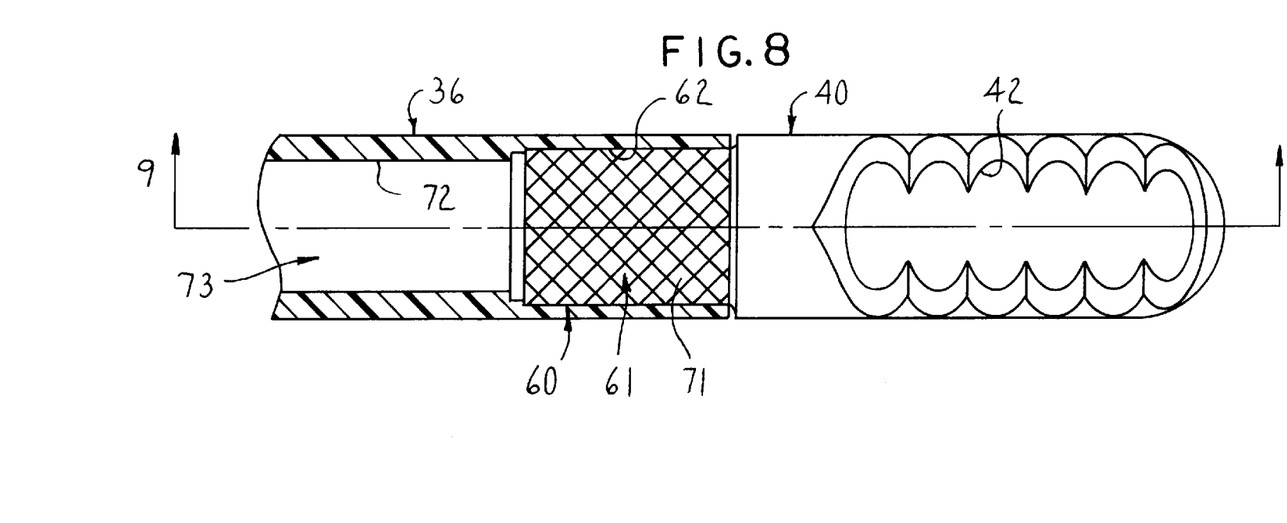
FIG. 8 is an enlarged view of the distal portion of the inner tubular member, taken from the top in FIG. 6, and showing the tip and, in central cross section, a fragment of the flexible tube of the inner tubular member.
Figure 9:
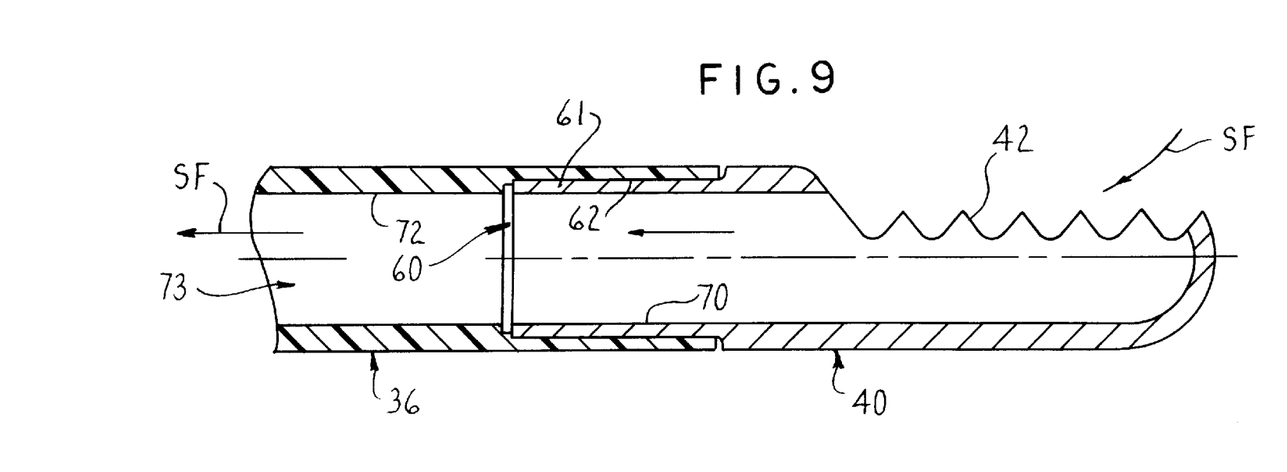
FIG. 9 is a sectional view substantially taken on the line 9—9 of FIG. 8.

The distal end portion 14 and tip 40 here have means, hereafter discussed more fully, for surgically working the tissue of a patient at a surgical site on the patient. Tools of the herein described type can be provided with a variety of different purpose, surgical tissue working means, including burs, cutters, etc. of conventional type. In the FIGS. 1 and 4 example, the distal end portion 14 of the outer tubular member 11 is provided with a laterally, and somewhat forwardly, opening window 41. The window 41 has laterally opposed cutting edges. The window 41 may be so formed by forming the distal end portion of the outer tubular member with a semi-spherical closed front end 43 and then machining away a part thereof, as here shown in FIG. 4. The inner tube tip 40 is rotatable snugly within the outer distal end portion 14 and has a similar window 42 (FIGS. 6, 8 and 9), also with laterally opposed cutting edges rotatable in shearing relation past the cutting edges of the window 41. The inner tubular member 30 is axially insertable forwardly into the outer tubular member 11 and is axially rearwardly removable therefrom when not installed on a handpiece HP. On the other hand, when installed on a handpiece HP, by rearward insertion into the forward extending chuck C thereof, the forward end of the shaft SH of the handpiece partly compresses the spring 35 (FIG. 1) of the drive hub 31, to push the tip 40 forward snugly against the front end 43 of the distal end portion 14 of the outer tubular member 11, so as to axially accurately position the tip 40 with respect to the outer end portion 14. This properly aligns the cutting edges of the windows 41 and 42 and maintains the proper relative axial position therebetween during cutting. Also, with the tool 11 installed in the handpiece HP, the diametral drive pin DP of the handpiece shaft enters and rides in a diametrally opposed pair of the notches 32 of the drive hub 31 and, upon rotation of the shaft SH, the drive pin DP correspondingly rotates the inner tubular member 30 and thereby rotates the tissue working tip 40 thereof to rotationally move the cutting edges of its window 42 past the corresponding cutting edges of the outer tubular member window 41.

Figure 6:
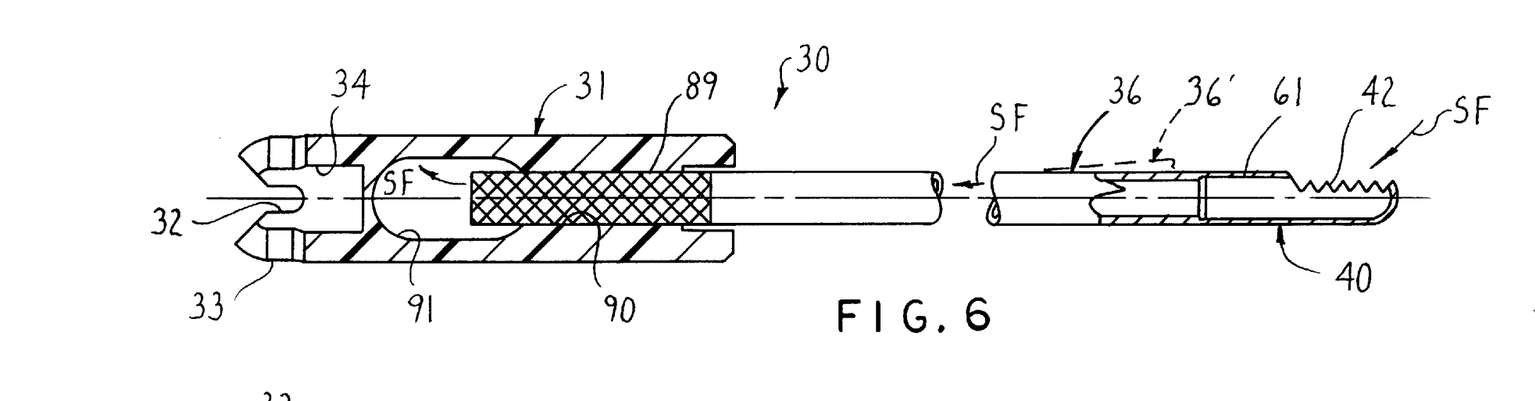
FIG. 6 is an enlarged side elevational view of the FIG. 1 inner tubular member broken away partially in central cross section.
Figure 7:
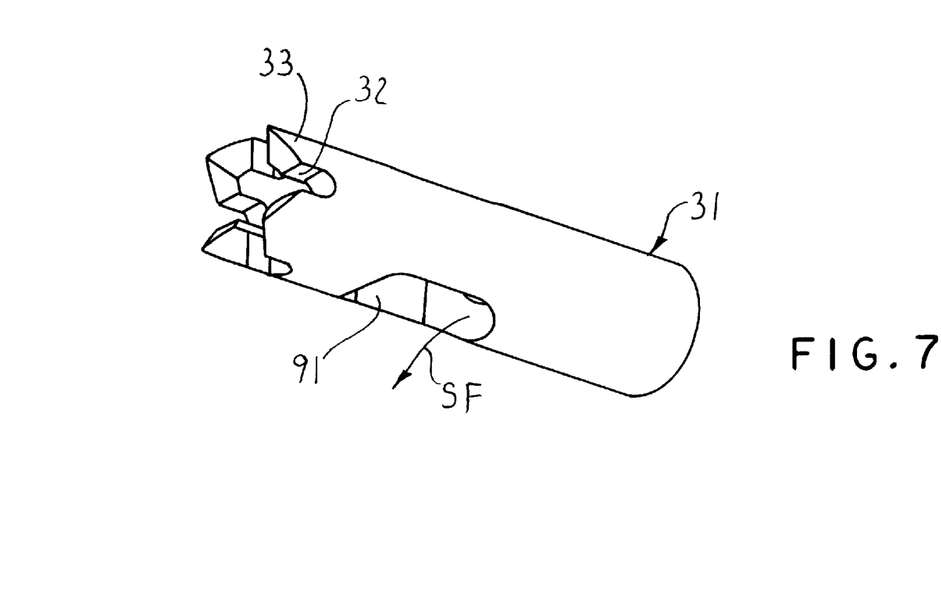
FIG. 7 is an enlarged pictorial view of the hub of the FIG. 6 inner tubular member.

In various surgical procedures, for example in trimming the edge of the meniscus cartilage in knee surgery, it is often desirable to irrigate the surgical site with liquid (in a conventional manner not shown) and then to draw flowable material (irrigation liquid, bits of removed tissue, etc.) from the surgical site by suction. This can be done by drawing such flowable material into the windows 41 and 42, then rearwardly along the length of the inner tubular member 30 and further rearwardly through a portion of the drive hub 31 and then radially outwardly into a suction path through the handpiece and outward therefrom to a suction source S, as schematically indicated by the suction flow arrows SF (FIGS. 1 and 6). Thus, the tool 10 can be used for simultaneously cutting tissue at the surgical site and removing flowable material from the surgical site.

To the extent above described, the tool is conventional. One example of such a tool is shown in above referenced Cezana et al. U.S. Pat. No. 5,192,292, assigned to the Assignee of the present invention.

Turning now more particularly to aspects of the present invention, the inner tube 36 (FIG. 6) is bendable and is of flexible polymer material. In one embodiment according to the invention, such polymer material is polyetheretherketone (PEEK). FIG. 6 schematically illustrates at 36' the ability of the inner tube 36 to bend as it rotates, to conform with a surrounding angled portion 50 (FIG. 1) of the outer tube 13. While the present invention can be used with both straight and angled outer tubes 13, the ability of the inner tube 36 to bend while rotating provides special advantages enabling it to be used with bent or bendable, angled tubes of the kind shown at 50 in FIG. 1.

The hollow interior of the tip extends from its cutting window 42 (FIG. 9) rearwardly through the annular flange 61 into communication with the bore 73 of the inner tube 36. The tip hollow interior and tube bore have substantially the same internal diameter and are coaxial to provide a substantially continuous interior wall along said tip and inner tube.

The tip 40 (FIGS. 8 and 9) has a reduced outside diameter, proximal end portion 60 defining a preferably cylindrical, annular flange 61 fixedly received within a preferably cylindrical, distal opening recess 62 of the inner tube 36 for fixing the tissue working tip 40 to the polymer inner tube 36.

Figure 10:
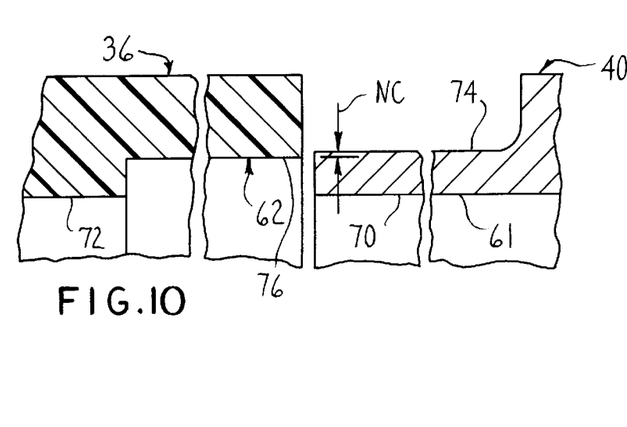
FIG. 10 is an enlarged fragment of the FIG. 9 tip and flexible tube shown axially exploded and immediately after formation of their respective annular flange and distal recess.

In the preferred embodiment shown in FIG. 10, the wall thickness of the inner tube 36, around the recess 62 is approximately two-thirds the wall thickness of the inner tube rearward of the recess 62, namely at its non-recessed inner peripheral wall 72. The ratio two-thirds may vary but preferably will be in the range of 60 to 75%.

Figure 13:
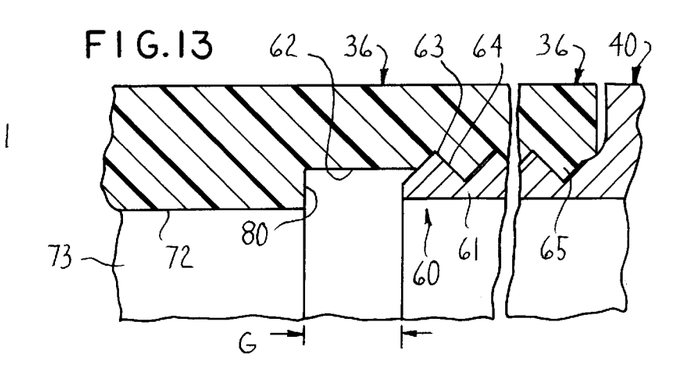
FIG. 13 is an enlarged fragment of FIG. 9, showing the tip annular flange and flexible tube recess in completed telescoped joinder.

The annular flange 61 is externally textured with hills 63 and valleys 64 (FIG. 13). The polymer material forming the inner wall of the inner tube 36 that defines recess 62 is shaped to have complementary hills 65 that seat in the valley of annular flange 62. The interlocking of the inner tube hills 65 in the flange valleys prevent rotational and axial relative movement of the tissue working tip 40 with respect to the inner tube 36. The polymer material of the inner tube 36 is flowed to form the hills 65 according to a method described hereinafter.

Figure 12:
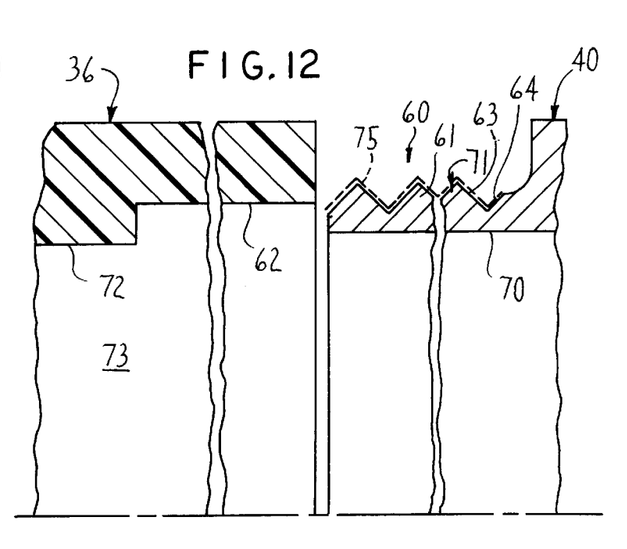
FIG. 12 is a view similar to FIG. 11 but showing the textured tip annular flange prior to telescoping in the inner tube distal recess.

In the preferred embodiment shown, the tissue working tip 40 is of stainless steel and the external texture on the annular flange 61, with its hills 63 and valleys 64, is a knurled pattern 71 on the outer periphery of the tip annular flange. The knurled pattern 71 extends substantially the circumference and length of the tip annular flange 61. In the preferred embodiment shown in FIG. 12, the radial depth from hill top to valley bottom is approximately, or at least approaches two-thirds, the maximum wall thickness of the thus textured annular flange 61 (i.e. the minimum annular flange thickness from valley bottom radially inward to the inner peripheral wall 70 of the annular flange 61 is about one-third the radial thickness from the peak of a hill 63 to such inner peripheral wall 70. The ratio two-thirds may vary but preferably will be in the range of 60 to 75%. The knurled pattern 71, defining the hills 63 and valleys 64, is somewhat schematically indicated in FIG. 8.

In the preferred embodiment shown, the tip 40 is fixed in the front end of the inner tube 36 as follows.

The tip 40 is formed as a generally bullet shaped hollow, rearward opening cup and the window 42 is machined in the forward portion of the tip. The rear peripheral portion of the tip 40 is machined to reduce the outside diameter thereof and thereby form the annular flange 61 (FIG. 10). The forward end portion of the inner tube 36 is machined at the inner peripheral wall 72 thereof to form the forward opening recess 62. The respective peripheral walls 74 and 76 of the annular flange 61 and recess 62 are substantially cylindrical and thus each have a substantial constant diameter. The outside diameter of the tip annular flange 61 is preferably slightly larger than the inside diameter of the recess 62 (for example about 0.010 inch in one unit constructed according to the invention, wherein the outside diameter of the outer tube 13 was about 4 mm). The result is a small negative clearance indicated at NC in FIG. 10.

Figure 11:
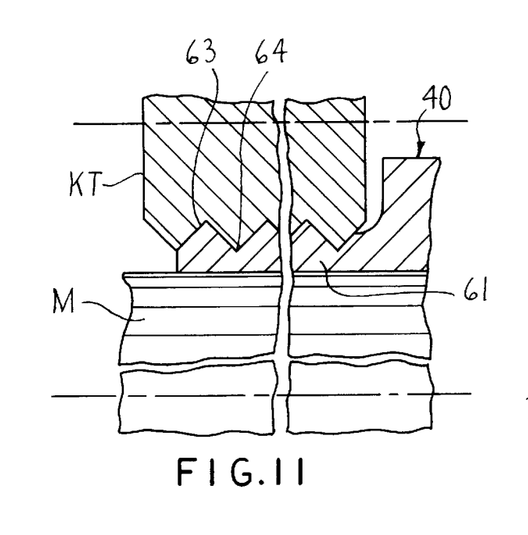
FIG. 11 is a view similar to FIG. 10 but showing a knurling tool and mandrel coacting with the tip annular flange to texture the outer periphery of the latter.

The outer periphery 74 (FIG. 10) of the tip annular flange 61 is externally textured by forming the hills 63 and valleys 64 (FIG. 11) therein. External texturing of the annular flange 61 is, in the preferred embodiment shown, accomplished by knurling. Because of the very small wall thickness of the annular flange 61 prior to knurling (0.0058 inch in one unit constructed according to the invention), a mandrel M (FIG. 11) is snugly but removably inserted within and radially supports the annular flange 61. Thereafter the tip 40 is rotated relative to a conventional knurling tool KT (FIG. 11) which bears radially inward against the outer periphery 74 of the annular flange to deform same, in a conventional knurling manner, to form the hills 63 and valleys 64. It will be understood that due to plastic deformation of the stainless steel material of the annular flange 61, the valleys 64 indent inward with respect to the original peripheral wall 74 of FIG. 10, while the hills 63 protrude outward with respect to such original peripheral wall 74. In one unit constructed according to the invention, the wall thickness of annular flange 61 at the hill peaks was about 0.0084 inch and at the valley bottoms was about 0.0032 inch, as compared to the original unknurled (as in FIG. 10) peripheral flange wall thickness of about 0.0058 inch. In the preferred embodiment shown in FIG. 12, the outside diameter of the knurled annular flange, at least at the peaks of the hills 63, exceeds the inside diameter of the recess 62 in the tube 36.

Thereafter, the tip 40, at least at its annular flange 61, is heated. The polymer inner tube 36 is of material of a thermoplastic character. The heated temperature of the tip annular flange 61 is sufficient to soften, and thus allow plastic flow of, the polymer material which bounds the perimeter of the inner tube recess 62 upon contact therewith.

The tip 40 and tube 36 are relatively moved coaxially to substantially fully insert the heated tip annular flange 61 in the tube recess 62 thereby causing the thermoplastic tube material bounding the recess 62 to flow around the hills 63 and into the valleys 64 of the heated annular flange 61 so as to form hills 65 (FIG. 13).

The tip 40 and inner tube 36 are then allowed to cool, thus substantially rigidifying the flowed thermoplastic material of the tube 36 around the hills 63 and in the valleys 64 of the annular flange 61 and therewith mechanically interlocking the tube 36 and tip 40 in axially and circumferentially fixed relation as seen in FIG. 13.

In one unit constructed according to the invention, this mechanical interlocking is aided, in fixing the tip 40 and tube 36 together, by applying a thin layer (schematically shown in dotted lines at 75 in FIG. 12) of a suitable adhesive, such as an epoxy adhesive, to the hills 63 and valleys 64 of the heated annular flange 61 prior to telescoping the annular flange 61 into the recess 62. The adhesive cures shortly after the FIG. 13 telescoped insertion is completed. Use of adhesive is optional, but such adhesive would desirably assist in compensating for recess and annular flange hill diameters that are respectively at the high and low ends of their respective clearance ranges and thus provide a looser than normal fit of annular flange 61 within recess 62.

In the preferred embodiment shown, the annular flange 61 is inserted in the tube recess 62 so as to leave an axial clearance gap G (FIG. 13) between the rear (left) end of the tip annular flange 61 and the opposed end face 80 the recess 62. In one unit constructed according to the invention, this clearance gap G was about 0.015 inch. The clearance gap G provides a predictable break point far to the rear of the windows 41 and 42, and indeed to the rear of the entire tip 40. In particular, the clearance gap G provides a minimum strength point along the length of the inner tubular member. Thus, if the tip, at its window 42, is accidentally jammed by a foreign object while rotating, thereby applying an excessive torque to the inner tube, the torque capability of the inner tubular member may be exceeded, causing it to circumferentially shear, and thus break into two pieces. Circumferential shear may occur by failure of the adhesive 75 (if any) and/or failure of the polymer material in the region of the tip hills 63 and valleys 64, thereby allowing the tip to rotate or even axially separate from the inner tube. If, the entire tip 40 does not separate from the inner tube 36, then the inner tube material at the clearance gap G will fail, in shear, allowing the entire tip 40, and the portion of the inner tube 36 surrounding it, to separate from the rearward portion of the inner tube 36, behind the gap G. In either event, the length of the separated front portion of the inner tubular member, namely the tip 40 as a whole, with or without surrounding material of the tubular member forward of the gap G, is too long to escape out of the window 41 of the outer tube 13 and hence cannot escape into the surgical site in the patient. Also, by selecting a particular maximum torque (e.g. in one unit constructed according to the invention 4 inch pounds of torque) at which the tip 40 will separate from the inner tube 36, in the manner above discussed, excessive torque accidentally applied to the cutting edges of the inner tubular member window 42 cannot tear apart, and hence fragment, the rotating tip 40. This prevents production of tip fragments small enough to escape through the outer tubular member window 41 and into the surgical site in the patient.

The shear strength of the polymer inner tube 36 at the gap G is substantially less than that of all parts of the stainless tip 40 despite the substantially smaller wall thicknesses of the stainless steel tip 40. The clearance gap G thus assures a piece separated from the inner tube 36, to the front end thereof, will be at least as long as the tip 40 and that such shearing would be of the polymer material of the inner tube 36 at the clearance gap G rather than for example, at the stress riser where the annular flange 61 joins the thicker front portion of the tip 40. This construction avoids problems present in certain prior art devices wherein the tip can be separated from its supporting inner tube in such a manner that it can easily be axially pulled away from the tube and wherein the tip itself is short enough to exit from the open front of the outer tube and fall into the surgical site.

In one inner tubular member constructed according to the invention, the maximum wall thickness of the polymer tube was about 0.0202 inch whereas the wall thickness at the recess was about 0.0135 inch. The outside diameter of the tube was about 0.1304 inch. In the same unit, the maximum wall thickness of the tip was about 0.0181 inch and the outside diameter of the tip was about 0.1292 inch.

To complete the assembly of the inner tube, the proximal end portion 89 of the inner tube 36 (FIG. 6) is fixed within a forward opening central passage 90 of the drive hub 31 and extends partly into a diametral suction port 91 which extends transversely through the drive hub 31.

In one unit constructed according to the invention, the inside diameter of the hub passage 90 was about 0.134 inch and the outside diameter of the unfinished inner tube 36 was about 0.132 inch, tolerances permitting a fit therebetween ranging from snug to interference. Prior to insertion of the inner tube 36 into the drive hub 31, the rear portion 89 of the inner tube 36 was textured, as by knurling, in the manner generally shown in FIG. 6. The knurling depth assures that the tops of the hills of the knurled portion 89 interfere somewhat with the peripheral wall of the drive hub passage 90 while the bottoms of the valleys of the knurled portion 89 are spaced from the interior peripheral wall of the drive hub passage 90. Preparatory to inserting into the drive hub 31, the inner tube rear end portion 89 was coated with a thin layer of adhesive, preferably epoxy resin. Thus, the friction fit between the inner tube knurled portion and hub 31 was assisted by an adhesive bond. This enables the drive hub 31 to inner tube 36 connection to withstand any torque, or axial separating pull, likely to be encountered in use and thereby effectively making the drive hub 31 and inner tube 36 one unit for all practical purposes. The drive hub 31, in the preferred embodiment shown, is of molded plastics material, preferably polycarbonate in one unit constructed according to the invention. Using a polycarbonate drive hub 31 and a PEEK inner tube 36, an epoxy adhesive was found to be compatible with both materials and to provide a rigid bond therebetween.

One unit constructed according to the invention, hereafter referred to as a 4 mm (millimeter) unit, utilized an outer tube 13 (FIG. 1) having an outside diameter of about 4 mm. However, the structure above described has been found to work well with tools in the 3.5 to 5.5 mm range. In tools below the 3.5 mm range, the inside diameter of the inner tube 36 is reduced enough that there may be risk of clogging during suction of fluent material from a surgical site, at least in some types of surgery. On the other hand, with an outer tube 13 having an outside diameter exceeding 5 or 5.5 mm, it may be difficult to maneuver the tool into a tight surgical site of the kind found in certain kinds of surgery. Accordingly, while the above described tool structure is useable in tools outside the range of 3.5 to 5.5 mm, that is a useful range (so as not to clog easily and yet penetrate tight surgical sites).

While the present invention has been illustrated herein in a angled cutter, it is contemplated that the present invention is also applicable to both straight and angled cutters, as well as to both straight and angled burs.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. A surgical tool for chucking in a powered surgical handpiece, said tool comprising:

an elongated outer tubular member having a proximal end adapted to be coupled to the surgical handpiece, and a distal end spaced from the proximal end, wherein a window is formed in the distal end; and an inner tubular member that is disposed in said outer tubular member and that is capable of rotation within said outer tubular member, said inner tubular member comprising:

a bendable inner tube of flexible polymer material, said inner tube having a proximal end and a distal end, a bore having a diameter that extends axially through said inner tube, a wall thickness around said bore, a recess that extends from the distal end a set length that is coaxial with said bore, said recess having a diameter that is greater than the diameter of said bore so that said inner tube has a wall thickness around said recess that is less than the wall thickness around said bore;

a drive hub fixed to the proximal end of said inner tube for engagement by a powered handpiece; and a tissue working tip extending forward from the distal end of said inner tube so as to be located adjacent said window of said outer tubular member, said tissue working tip having a reduced diameter proximal end portion defining an annular flange, said annular flange being seated in said recess of said inner tube wherein, said annular flange extends a distance into said recess less than the length of said recess so that said inner tube, between said bore and said annular flange, has an unreinforced section of reduced wall thickness.

2. The apparatus of claim 1, in which said annular flange of said tissue working tip is externally textured with hills and valleys and said inner tube has an inner wall that defines said recess, said inner wall having hills that seat in said valleys of said annular flange to form a mechanical interlock against rotational and axial relative movement of said tissue working tip with respect to said tube.

3. The apparatus of claim 2 in which said external texture of said annular flange of said tissue working tip, with its hills and valleys, is a knurled surface on the periphery of said annular flange.

4. The apparatus of claim 3, in which said knurled surface extends substantially the circumference and length of said annular flange of said tissue working tip.

5. The apparatus of claim 4, in which said tissue working tip is of stainless steel.

6. The apparatus of claim 2 in which said polymer material is PEEK (polyetheretherketone).

7. The apparatus of claim 2, in which said hill and valley depth of said annular flange of said tissue working tip is approximately two-thirds the wall thickness of said annular flange.

8. The apparatus of claim 2, wherein said inner tube has a wall thickness around said recess that is between 60 and 75% the wall thickness of said inner tube around said bore.

9. The apparatus of claim 2 in which said outer tubular member has an angled portion between its ends, said inner tube being bendable at least at the portion thereof received in the angled portion of said outer tubular member.

10. The apparatus of claim 2, further including an adhesive material disposed over said hills and valleys of said annular flange of said tissue working tip so as to form an adhesive bond between said inner tube and said tissue working tip.

11. The apparatus of claim 1, wherein substantially all of said annular flange of said tissue working tip is seated in said recess of said inner tube.

12. An inner tubular member for placement in an outer tubular member for use with a powered surgical handpiece, said inner tubular member comprising:

a bendable inner tube of flexible polymer material, said inner tube having a proximal end and a distal end, a bore having a diameter that extends axially through said inner tube, a wall thickness around said bore and a recess that extends from the distal end a set length that is coaxial with said bore, said recess having a diameter that is greater than the diameter of said bore so that said inner tube has a wall thickness around said recess that is less than the wall thickness around said bore;

a drive hub fixed to the proximal end of said inner tube for engagement by a powered handpiece; and a tissue working tip extending forward from the distal end of said inner tube, said tissue working tip having a reduced diameter proximal end portion defining an annular flange, said annular flange being seated in said recess of said inner tube wherein said annular flange extends a distance into said recess less than the length of said recess so that said inner tube, between said bore and said annular flange, has an unreinforced section of reduced wall thickness.

13. The apparatus of claim 12, in which said annular flange is externally textured with hills and valleys and said inner tube has an inner wall that defines said recess, said inner wall having hills that seat in said valleys of said annular flange to form a mechanical interlock against rotational and axial relative movement of said tip with respect to said tube.

14. The apparatus of claim 13 in which said external texture of said annular flange of said tissue working tip, with its hills and valleys, is a knurled surface.

15. The apparatus of claim 13 in which said external texture of said annular flange of said tissue working tip is integral with and a continuous radially outward extension of the material of said annular flange.

16. The apparatus of claim 13 in which said external texture of said annular flange of said tissue working tip is circumferentially continuous, so as to continue through the full 360° circumference of said annular flange.

17. The apparatus of claim 13, further including an adhesive material disposed over said hills and valleys of said annular flange so as to form an adhesive bond between said inner tube and said tissue working tip.

18. The apparatus of claim 12, wherein substantially all of said annular flange of said tissue working tip is seated in said recess of said inner tube.

* * * * *

UNITED STATES PATENT AND TRADEMARK OFFICE
CERTIFICATE OF CORRECTION

PATENT NO : 5,961,532
DATED : October 5, 1999
INVENTOR(S) : Marshal E. FINLEY et al It is certified that error appears in the above-identified patent and that said Letters Patent is hereby corrected as shown below:

Column 9, line 19; change "Claim 2" to ---Claim 1---.

Signed and Sealed this

Eighteenth Day of April, 2000

Attest:

Q. TODD DICKINSON

*Attesting Officer*     *Director of Patents and Trademarks*